(12) United States Patent
Takahashi et al.

(10) Patent No.: US 11,513,075 B2
(45) Date of Patent: Nov. 29, 2022

(54) OBSERVATION DEVICE AND OBSERVATION METHOD

(71) Applicant: HAMAMATSU PHOTONICS K.K., Hamamatsu (JP)

(72) Inventors: Akira Takahashi, Hamamatsu (JP); Shunsuke Matsuda, Hamamatsu (JP); Takayuki Miyashita, Hamamatsu (JP); Mitsuharu Miwa, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 718 days.

(21) Appl. No.: 16/478,859

(22) PCT Filed: Oct. 12, 2017

(86) PCT No.: PCT/JP2017/037052
§ 371 (c)(1),
(2) Date: Jul. 18, 2019

(87) PCT Pub. No.: WO2018/135051
PCT Pub. Date: Jul. 26, 2018

(65) Prior Publication Data
US 2019/0376893 A1  Dec. 12, 2019

(30) Foreign Application Priority Data
Jan. 19, 2017 (JP) .............................. JP2017-007384

(51) Int. Cl.
*G01J 3/44* (2006.01)
*G01N 21/64* (2006.01)
(Continued)

(52) U.S. Cl.
CPC ........... *G01N 21/64* (2013.01); *A61B 5/0059* (2013.01); *G01N 21/27* (2013.01)

(58) Field of Classification Search
CPC .......... G01J 3/26; G01N 21/64; G01N 21/27; A61B 5/0059; A61B 5/0071; A61B 10/00; G02B 21/36
See application file for complete search history.

(56) References Cited

U.S. PATENT DOCUMENTS 7,897,937 B2 * 3/2011 Engelhardt ........ G01N 21/6428
250/459.1
2003/0158470 A1 * 8/2003 Wolters ................ A61B 5/0084
600/317

(Continued)

FOREIGN PATENT DOCUMENTS

CN 1886689 A 12/2006
CN 102282456 A 12/2011

(Continued)

OTHER PUBLICATIONS

International Preliminary Report on Patentability (IPRP) dated Aug. 1, 2019 that issued in WO Patent Application No. PCT/JP2017/037052.

*Primary Examiner* — Abdullahi Nur
(74) *Attorney, Agent, or Firm* — Faegre Drinker Biddle & Reath LLP

(57) ABSTRACT

An observation device is an observation device observing an observation target and includes: an emission light source that generates emission light; a projection light source that generates projection light; a scanning mirror that scans the emission light and the projection light toward the observation target along the same optical path; a light guide optical system that guides detection target light generated in the observation target in accordance with emission of the emission light without it passing through the scanning mirror; an optical detector that detects the detection target light guided by the light guide optical system; and a control unit that (Continued)

controls an intensity of the projection light on the basis of a result of the detection of the detection target light.

23 Claims, 6 Drawing Sheets

(51) Int. Cl.
 A61B 5/00 (2006.01)
 G01N 21/27 (2006.01)

(56) References Cited

U.S. PATENT DOCUMENTS

| | | | |
|---|---|---|---|
| 2010/0046039 A1* | 2/2010 | Xie | G01J 3/44 |
| | | | 356/301 |
| 2010/0134608 A1* | 6/2010 | Shibasaki | G02B 23/2423 |
| | | | 348/E7.085 |
| 2010/0157039 A1* | 6/2010 | Sugai | A61B 1/07 |
| | | | 348/E7.085 |
| 2014/0187966 A1 | 7/2014 | Thierman | |
| 2015/0054938 A1* | 2/2015 | Suzuki | G06T 7/97 |
| | | | 348/80 |
| 2016/0095661 A1* | 4/2016 | Rephaeli | A61B 5/0071 |
| | | | 606/3 |

FOREIGN PATENT DOCUMENTS

| | | |
|---|---|---|
| CN | 102985866 A | 3/2013 |
| CN | 104939802 A | 9/2015 |
| JP | 2006-003747 A | 1/2006 |
| JP | 2006-301541 A | 11/2006 |
| JP | 2015-524578 A | 8/2015 |
| JP | 2016-27367 A | 2/2016 |
| WO | WO 2010/087251 A1 | 8/2010 |
| WO | WO 2010/134351 A1 | 11/2010 |
| WO | WO-2014/015128 A2 | 1/2014 |
| WO | WO 2014/076993 A1 | 5/2014 |
| WO | WO 2017/097601 A1 | 6/2017 |

* cited by examiner

OBSERVATION DEVICE AND OBSERVATION METHOD

TECHNICAL FIELD

This embodiment relates to an observation device and an observation method.

BACKGROUND ART

As a conventional observation device, for example, there is a projection system disclosed in Patent Literature 1. This projection system is configured as an operation support system and includes an infrared excitation light source that emits excitation light toward an affected part of a patient, an infrared camera that images fluorescence occurring in the affected part in accordance with emission of excited light, a projection unit that projects a projection image based on a result of the imaging of fluorescence to an affected part, and the like.

CITATION LIST

Patent Literature

[Patent Literature 1] Japanese Unexamined Patent Publication No. 2016-27367

SUMMARY OF INVENTION

Technical Problem

In the conventional observation device described above, it is assumed that light from an infrared excitation light source is emitted toward an affected part in a wide area, a TOF sensor is disposed for adjustment of a projection image, and the projection image is controlled in accordance with a distance to the affected part. For this reason, the device becomes complicated, and complex arithmetic operations are necessary for reflecting results of the imaging of fluorescence in a projection image.

This embodiment is realized for solving the problems described above, and an object thereof is to provide an observation device and an observation method capable of displaying a projection image in an observation target without requiring complex arithmetic operations by a simple configuration.

Solution to Problem

An observation device according to this embodiment is an observation device for observing an observation target and includes: a first light source that generates emission light; a second light source that generates projection light; an optical scanning device that scans the emission light and the projection light toward the observation target along the same optical path; a light guide optical system that guides detection target light generated in the observation target in accordance with emission of the emission light without it passing through the optical scanning device; an optical detector that detects the detection target light guided by the light guide optical system; and a control unit that controls an intensity of the projection light on the basis of a result of the detection of the detection target light.

In this observation device, the emission light and the projection light are scanned toward the observation target along the same optical path, and detection target light that is transmitted from the observation target is detected without it passing through the optical scanning device (without descanning). By transmitting the emission light and the projection light along the same optical path, the device configuration is simplified. In addition, the emission positions of the emission light and the projection light on the observation target coincide with each other, and accordingly, an arithmetic operation for reflecting results of the detection of the detection target light in a projection image becomes simplified.

In addition, an optical axis of an optical scanning system including the optical scanning device and an optical axis of the light guide optical system may coincide with each other. In such a case, the device configuration is further simplified. Furthermore, even in a case in which an observation target moves in the direction of the optical axis, the influence thereof on observation can be reduced.

In addition, an optical axis of an optical scanning system including the optical scanning device and an optical axis of the light guide optical system may not coincide with each other. In such a case, an optical device that splits the emission light and the projection light and detection target light from each other is not necessary, and accordingly, a more sufficient amount of detection target light can be secured.

In addition, the emission light may be excitation light. In such a case, a fluorescent material is excited by the emission light, and fluorescence observation of the observation target can be performed.

In addition, a wavelength of the emission light may be 400 nm to 810 nm. In this wavelength band, representative fluorescent materials such as indocyanine green, methylene blue, fluorescein, and 5-aminolevulinic acid can be excited using the emission light.

In addition, a wavelength of the emission light may be a wavelength that can be absorbed by the observation target. In such a case, observation of the observation target based on absorption of emission light can be performed.

In addition, the wavelength of the emission light may be 735 nm to 850 nm. In this wavelength band, for example, emission light can be absorbed in blood vessels (or blood).

In addition, a wavelength of the projection light may be a wavelength different from a wavelength of the emission light. In such a case, emission light and projection light can be differentiated on the observation target.

In addition, the wavelength of the projection light may be 380 nm to 780 nm. In this wavelength band, a projection image according to the projection light can be displayed with high visibility in an observation target.

In addition, the optical detector may be a single point sensor. In this way, the detection rate in the optical detector can be raised, and real-time processing of projection light can be performed by the control unit.

In addition, the observation device may further include an image generating unit that generates an image on the basis of a result of the detection of the detection target light. In such a case, display of a result of the detection on a display, storage of a result of the detection in an external storage device, and the like can be performed.

In addition, a field of view of the light guide optical system may include a scanning range of the emission light according to the optical scanning device. In such a case, a projection image can be projected over the scanning range of the emission light according to the optical scanning device.

In addition, an observation method according to one aspect of the present invention is an observation method for observing an observation target, the observation method including: a first light generating step of generating emission light; a second light generating step of generating projection light; an optical scanning step of scanning the emission light and the projection light toward the observation target along the same optical path using an optical scanning device; a light guiding step of guiding detection target light generated in the observation target in accordance with emission of the emission light without it passing through the optical scanning device using a light guide optical system; a detection step of detecting the detection target light guided by the light guide optical system using an optical detector; and a control step of controlling an intensity of the projection light on the basis of a result of the detection of the detection target light in the detection step.

In this observation method, the emission light and the projection light are scanned toward the observation target along the same optical path, and detection target light that is transmitted from the observation target is detected without it passing through the optical scanning device (without descanning). By transmitting the emission light and the projection light along the same optical path, the device configuration is simplified. In addition, the emission positions of the emission light and the projection light on the observation target coincide with each other, and accordingly, an arithmetic operation for reflecting results of the detection of the detection target light in a projection image becomes simplified.

In addition, an optical axis of an optical scanning system including the optical scanning device and an optical axis of the light guide optical system may be caused to coincide with each other. In such a case, the device configuration is further simplified. Furthermore, even in a case in which an observation target moves in the direction of the optical axis, the influence thereof on observation can be reduced.

In addition, an optical axis of an optical scanning system including the optical scanning device and an optical axis of the light guide optical system may be caused not to coincide with each other. In such a case, an optical device that splits the emission light and the projection light and detection target light from each other is not necessary, and accordingly, a sufficient amount of the detection target light can be secured.

In addition, the emission light may be excitation light. In such a case, a fluorescent material is excited by the emission light, and fluorescence observation of the observation target can be performed.

In addition, a wavelength of the emission light may be set to be 400 nm to 810 nm. In this wavelength band, representative fluorescent materials such as indocyanine green, methylene blue, fluorescein, and 5-aminolevulinic acid can be excited using the emission light.

In addition, a wavelength of the emission light may be set to be a wavelength that can be absorbed by the observation target. In such a case, observation of the observation target based on absorption of emission light can be performed.

In addition, the wavelength of the emission light may be set to be 735 nm to 850 nm. In this wavelength band, for example, emission light can be absorbed in blood vessels (or blood).

In addition, a wavelength different from a wavelength of the emission light may be set as a wavelength of the projection light. In such a case, emission light and projection light can be differentiated on the observation target.

In addition, the wavelength of the projection light may be set to be 380 nm to 780 nm. In this wavelength band, a projection image according to the projection light can be displayed with high visibility in an observation target.

In addition, a single point sensor may be used as the optical detector. In this way, the detection rate in the optical detector can be raised, and real-time processing of projection light can be performed by the control unit.

In addition, the observation method may further include an image generating step of generating an image on the basis of a result of the detection of the detection target light. In such a case, display of a result of the detection on a display, storage of a result of the detection in an external storage device, and the like can be performed.

In addition, a field of view of the light guide optical system may include a scanning range of the emission light according to the optical scanning device. In such a case, a projection image can be projected over the scanning range of the emission light according to the optical scanning device.

Advantageous Effects of Invention

According to such an observation device and an observation method, a projection image can be displayed in an observation target without requiring complex arithmetic operations by a simple configuration.

DESCRIPTION OF EMBODIMENTS

Hereinafter, preferred embodiments of an observation device and an observation method according to one aspect of the present invention will be described in detail with reference to the drawings.

First Embodiment

Figure 1:
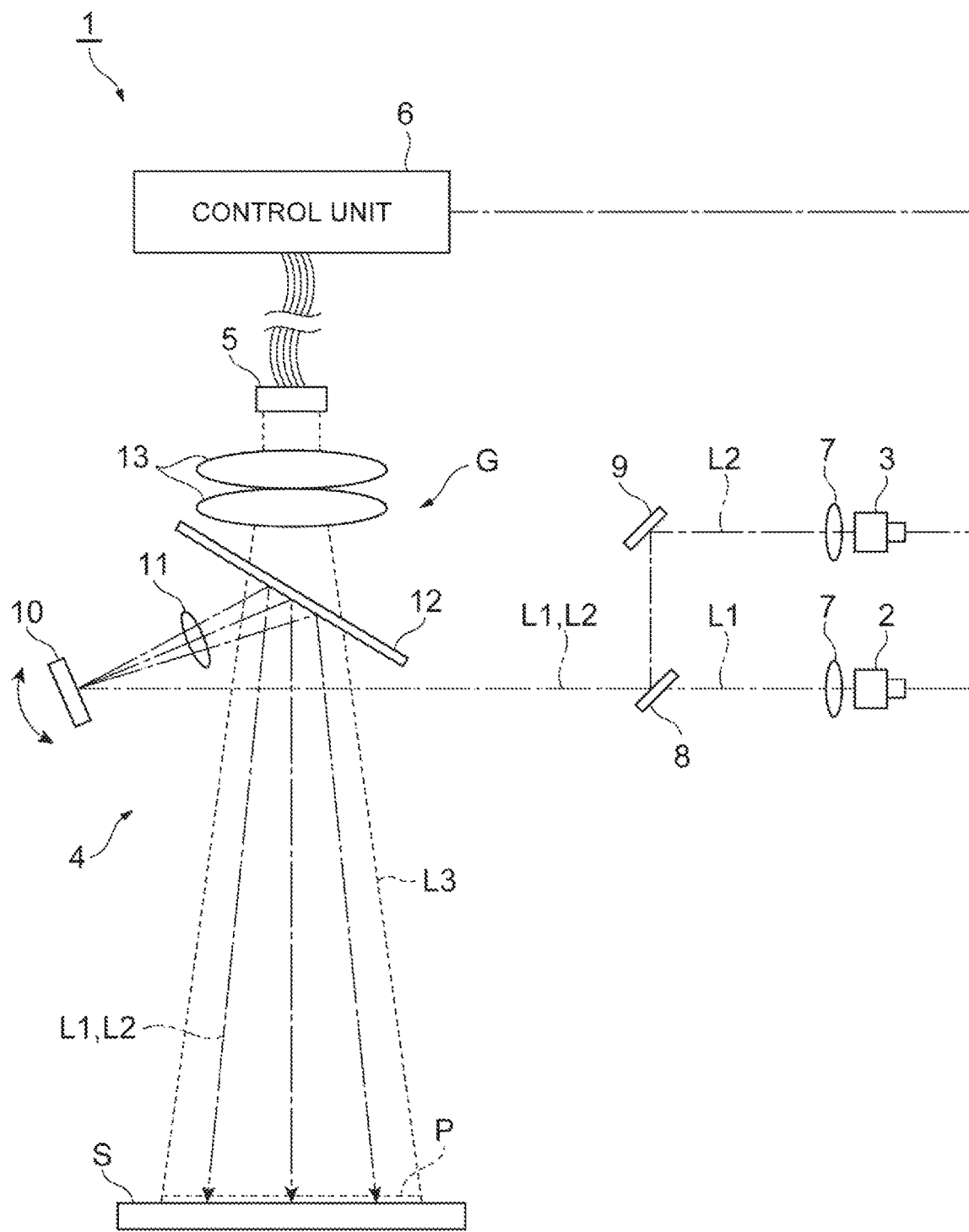
FIG. 1 is a schematic configuration diagram illustrating an observation device according to a first embodiment.

FIG. 1 is a schematic configuration diagram illustrating an observation device according to a first embodiment. The observation device 1 illustrated in the drawing is a device that allows observation of an observation target S. In this embodiment, the observation target S is a biological tissue into which a fluorescent material has been injected, and the observation device 1 is configured as a device that allows observation of a state of a biological tissue through fluorescent observation in real time. An operation distance of the observation device 1 (a preferred distance from the device to an observation target S for appropriate observation), for example, is about 10 cm to 20 cm but is not limited thereto. In addition, the observation device 1 has a function of improving visibility of an observation result on the observation target S by displaying a projection image P based on a result of detection of fluorescence on the observation target S.

As a fluorescent material used for fluorescence observation, for example, there is indocyanine green. Indocyanine green is excited by infrared light and emits infrared fluorescence having a wavelength different from the excitation light. Both the excitation light and infrared fluorescence can be easily transmitted through a biological tissue and thus are appropriate for fluorescence observation of a deep part of a biological tissue. As other pigments, for example, there are methylene blue, fluorescein, 5-aminolevulinic acid, and the like.

As illustrated in FIG. 1, the observation device 1 includes an emission light source (first light source) 2 that generates emission light L1, a projection light source (second light source) 3 that generates projection light L2, an optical scanning system 4 that scans the emission light L1 and the projection light L2, a light guide optical system G that guides detection target light L3 from an observation target S, an optical detector 5 that detects the detection target light L3 that has been guided, and a control unit 6 that controls an operation of the device.

The emission light source 2 is a light source that emits excitation light including a wavelength exciting fluorescence as emission light L1. In the examples of the fluorescent material, an excitation wavelength of indocyanine green is about 775 nm, an excitation wavelength of methylene blue is about 670 nm, an excitation wavelength of fluorescein is about 495 nm, and an excitation wavelength of 5-aminolevulinic acid is about 405 nm. Accordingly, the wavelength of the emission light L1, for example, is selected from a band of 400 nm to 810 nm. In a case in which indocyanine green is used as a fluorescent material, for example, a semiconductor laser that outputs laser light having a wavelength of 785 nm is used as the emission light source 2. In addition, not only a coherent light source such as a laser but also an incoherent light source such as an LED or a super luminescent diode (SLD) may be used as the emission light source 2.

The projection light source 3 is a light source that emits visible light including a wavelength different from that of the emission light L1 as the projection light L2. The wavelength of the projection light L2, for example, is selected from a band of 380 nm to 780 nm that is a visible band. In a case in which laser light having a wavelength of 785 nm is used as the emission light L1, for example, a semiconductor laser that outputs laser light having a wavelength of 580 nm is used as the projection light source 3. In addition, not only a coherent light source such as a laser but also an incoherent light source such as an LED or an SLD may be used as the projection light source 3.

In each of the emission light source 2 and the projection light source 3, an aperture used for adjustment of a beam diameter and prevention of stray light from the outside may be disposed. The aperture may have an invariable opening diameter or a variable opening diameter. In addition, a plurality of apertures having different opening diameters may be disposed, and an aperture having a different opening diameter according to conditions of detection may be selectively used. Furthermore, a collimator lens 7 may be disposed in each of the emission light source 2 and the projection light source 3. In such a case, the emission light L1 and the projection light L2 are guided to the optical scanning system 4 in a parallelized-light state by the collimator lens 7.

The optical scanning system 4 is an optical system that scans the emission light L1 and the projection light L2 toward an observation target S in the same optical path. The optical scanning system 4, for example, is composed of a dichroic mirror 8, a mirror 9, a scanning mirror (optical scanning device) 10, a condensing lens 11, and a beam splitter 12. The emission light L1 generated by the emission light source 2 passes through the dichroic mirror 8 and is incident to the scanning mirror 10. The projection light L2 generated by the projection light source 3 is reflected by the dichroic mirror 8 and the mirror 9, passes through the same optical path as that of the emission light L1, and is incident to the scanning mirror 10.

The scanning mirror 10 is a mirror that scans the emission light L1 and the projection light L2 incident in the same optical path in one axis or two axes with respect to an observation target S. The driving of the scanning mirror 10 is controlled on the basis of a control signal transmitted from the control unit 6. As the scanning mirror 10, for example, an MEMS mirror, a galvanomirror, a polygon mirror, or the like can be used. Instead of the scanning mirror 10, a different optical device such as a spatial light modulator may be used as an optical scanning device. In addition, the beam splitter 12 is a device that reflects the emission light L1 and the projection light L2 and transmits detection target light L3, which is generated in an observation target S, in accordance with the emission of the emission light L1. As the beam splitter 12, for example, a dichroic mirror or a half mirror can be used. In addition, depending on the optical arrangement, the beam splitter 12 may reflect the detection target light L3 while transmitting the emission light L1 and the projection light L2.

The emission light L1 and the projection light L2 reflected by the scanning mirror 10 are condensed by the condensing lens 11, are reflected by the beam splitter 12, and are incident to the observation target S with the same optical path maintained. In other words, the emission light L1 and the projection light L2 are incident to the same position on the observation target S. In this embodiment, the emission light L1 and the projection light L2 are reflected by the beam splitter 12 and thereafter are incident to the observation target S approximately perpendicularly.

The light guide optical system G is an optical system that guides the detection target light L3, which is generated on an observation target S in accordance with the emission of the emission light L1, to the optical detector 5. The light guide optical system G, for example, is composed of the beam splitter 12 and the observation lens 13. In this embodiment, the optical axis of the optical scanning system 4 and the optical axis of the light guide optical system G are adjusted such that they become the same axis. The observation lens 13, for example, is composed of a plurality of convex lenses. The observation lens 13 condenses detection target light L3 which diffuses from a generation position on the observation target S.

By condensing the detection target light L3 using the observation lens 13, a more sufficient amount of the detection target light L3, which is detected by the optical detector 5, can be secured. In addition, the size of the field of view of the light guide optical system G can be adjusted using the observation lens 13. The observation lens 13 may have a configuration in which condensation of the detection target light L3 can be supported, and the optical detector 5 does not necessarily need to be disposed at a focal position of the observation lens 13. In addition, the light guide optical system G may include a filter having a transmission band corresponding to the wavelength band of the detection target light L3. As examples of such a filter, there are a long path filter, a band pass filter, and the like.

When emission light L1 is incident and scanned, at a position at which a fluorescent material is present (included) inside the observation target 5, the fluorescent material is excited by the emission light L1, and fluorescence is generated as detection target light L3. In this case, the detection target light L3 diffuses radially from a generation position (an emission position of the emission light L1) on the observation target S. This detection target light L3 is transmitted through the beam splitter 12 and is incident to the optical detector 5 side without it passing through the scanning mirror 10 (without being reflected on the scanning mirror 10). In other words, the light guide optical system G guides the detection target light L3 to the optical detector 5 without it passing through the scanning mirror 10.

In addition, in accordance with emission and scanning of the projection light L2, a projection image P is projected onto the surface of the observation target S. By projecting the projection image P to the observation target S, a position at which fluorescence is generated on the observation target S can be visually recognized. It is preferable to set a field of view (observation range) of the light guide optical system G such that it includes a scanning range of the emission light L1 according to the optical scanning system 4. In such a case, the projection image P can be projected over the scanning range of the emission light L1 according to the optical scanning system 4.

The optical detector 5 detects the detection target light L3 which is guided by the light guide optical system G The optical detector 5, for example, is composed of a photo-diode, an avalanche photo-diode, a photomultiplier tube, a silicon photomultipliers (SiPM), or the like. The optical detector 5 detects the detection target light L3 and outputs a detection signal (information representing a result of detection) to the control unit 6.

In this embodiment, the observation target S and the optical detector 5 have an arrangement that has no image formation relation therebetween. For this reason, even in a case in which a position at which detection target light L3 on the observation target S is generated is moved by the scanning mirror 10, the detection target light L3 is guided to the optical detector 5. Accordingly, in this embodiment, it is preferable that a single point sensor having a high detection rate is used as the optical detector 5.

For example, the control unit 6 is a computer that is physically configured to include memories such as a RAM, a ROM, and the like, a processor (an arithmetic operation circuit) such as a CPU or the like, a communication interface, a storage unit such as a hard disk, and a data input/output unit that performs input/output of data for an external medium such as a USB memory or the like. The computer may be configured to further include a display unit such as a display or the like. As examples of such a computer, there are a personal computer, a cloud server, a smart device (a smartphone, a tablet terminal, or the like), a microcomputer, a field-programmable gate array (FPGA), and the like. The computer executes a program stored in a memory using a CPU, thereby executing various control functions.

When an input of starting an operation is accepted from an outside, the control unit 6 starts to drive the emission light source 2, the projection light source 3, and the scanning mirror 10. In addition, when information representing a result of detection of detection target light L3 is received from the optical detector 5, the control unit 6 forms a projection image P on which the result of detection is reflected on the surface of the observation target S by controlling the intensity of the projection light L2 generated from the projection light source 3 on the basis of the result of detection of the detection target light L3. The control of the intensity of the projection light L2 is performed in accordance with conditions such as the type of an observation target S, the kind of a fluorescent material, and the wavelength of projection light L2.

The control unit 6 may perform control of the projection light source 3 such that the intensity of the projection light L2 is proportional to the detected intensity of the detection target light L3 or may perform control of the projection light source 3 such that the intensity of the projection light L2 becomes nonlinear with respect to the detected intensity of the detection target light L3 by performing γ correction of the intensity of the projection light L2. In addition, the control unit 6 may perform switching between on/off of the projection light source 3 on the basis of the detected intensity of the detection target light L3 with respect to a threshold set in advance or may set two different thresholds and perform switching between on/off of the projection light source 3 on the basis of whether or not the detected intensity of the detection target light L3 is within a range of the two thresholds.

Instead of directly controlling the intensity of the projection light L2, the control unit 6 may control the repetition frequency of the pulse of the projection light L2. Since the eyes of a person perceive projection light L2 by integrating a plurality of pulses, even in a case in which the repetition frequency of the pulse of projection light L2 is changed without changing the intensity, visual effects similar to those of a case in which the intensity of the projection light L2 is changed can be acquired. In addition, the control unit 6 may perform control of the projection light source 3 such that the projection light L2 is emitted only to a predetermined area of the observation target S. For example, by emitting the projection light L2 only to the contour of an area in which fluorescence is detected, the amount of energy of laser light emitted to the observation target S can be decreased. In this way, a damage on the observation target S decreases, or the power consumption of the observation device 1 can be reduced.

The control unit 6 may execute a background subtraction process of the detection target light L3 by controlling the intensity of the projection light L2. The background subtraction process, for example, is a process of detecting an intensity of the background of the observation target S in a state in which the emission light source 2 is off and subtracting the intensity of the background from the intensity of the detection target light L3 at the time of detecting the detection target light L3. In this case, detection of the background, for example, may be performed for each scanning line according to the scanning mirror 10.

In addition, detection of a background may be performed by performing laser modulation of the emission light L1 and subtracting a detected intensity detected when the emission light L1 is off from a detected intensity detected when the emission light L1 is on for each pixel of a scanning area according to the scanning mirror 10. A detection period of a background may be set as a return period of scanning of the scanning mirror 10. In such an example, emission of the projection light L2 may be performed at the same time.

Next, the operation of the observation device 1 will be described.

Figure 2:
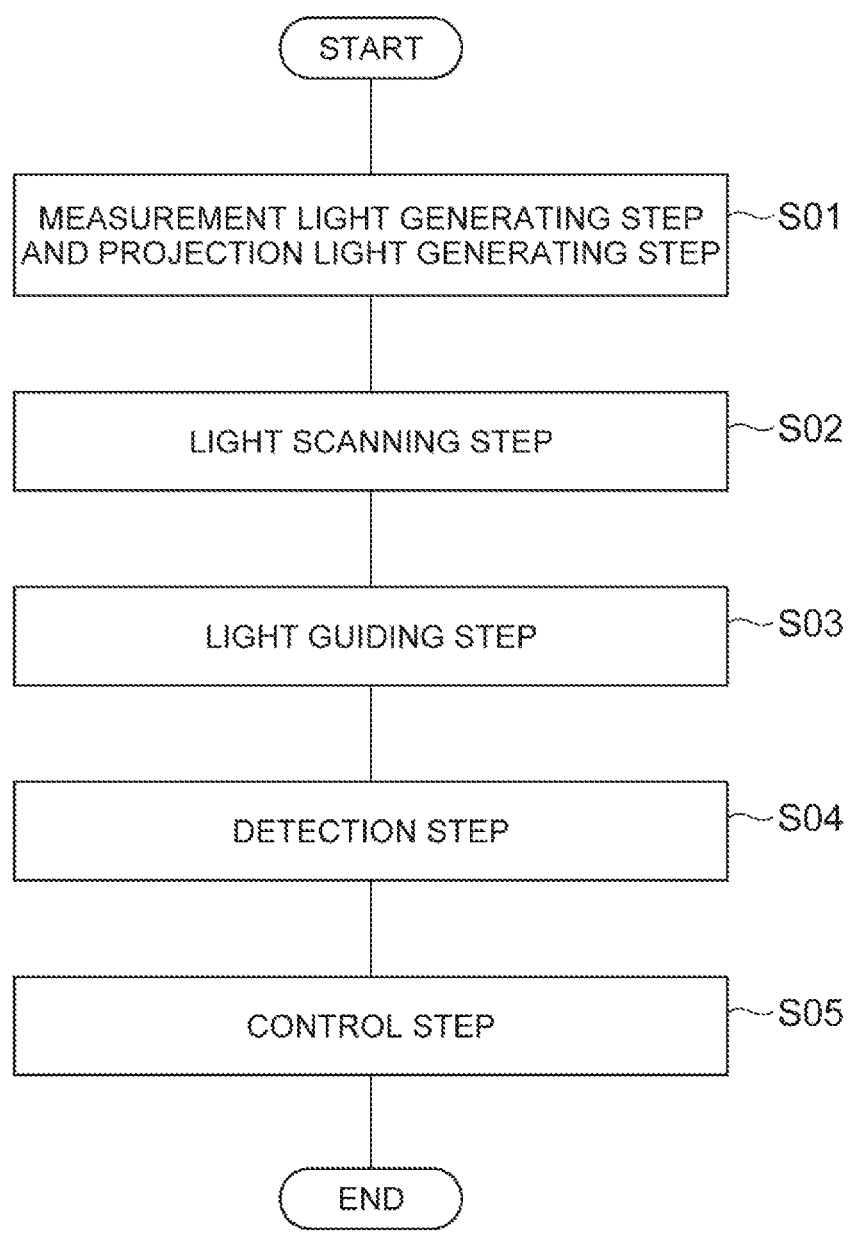
FIG. 2 is a flowchart illustrating an operation of the observation device illustrated in FIG. 1.

FIG. 2 is a flowchart illustrating an operation of the observation device 1. As illustrated in the same drawing, in the observation device 1, when an operation for starting observation is input, emission light L1 is generated from the emission light source 2, and projection light L2 is generated from the projection light source 3 (Step S01: an emission light generating step (first light generating step) and a projection light generating step (second light generating step)). The emission light L1 and the projection light L2 are guided to the same optical path in the optical scanning system 4 and are scanned toward an observation target S by the scanning mirror 10 with the same optical path maintained (Step S02: an optical scanning step). According to emission and scanning of the emission light L1, fluorescence is generated in accordance with excitation of a fluorescent material on the observation target S. In addition, according to the emission and the scanning of the projection light L2, a projection image P is formed on the surface of the observation target S.

Next, in the observation device 1, the fluorescence generated by the observation target S is guided to the optical detector 5 through the scanning mirror 10 as detection target light L3 (Step S03: a light guiding step). The detection target light L3 guided in the light guiding step S03 is detected by the optical detector (Step S04: a detection step). Then, information representing a result of detection of the detection target light L3 is output to the control unit 6, and an intensity of the projection light L2 is controlled on the basis of a result of detection of the detection target light L3 that is acquired by the optical detector 5 (Step S05: a control step). In this way, a projection image P on which the result of detection of the detection target light L3 is reflected is formed on the surface of the observation target S.

As described above, in this observation device 1, the emission light L1 and the projection light L2 are scanned toward the observation target S along the same axis, and detection target light L3 that is transmitted from the observation target S is detected without it passing through the optical scanning system 4 (without descanning). In this way, by transmitting the emission light L1 and the projection light L2 along the same optical path, the device configuration is simplified, and, compared to a case in which the emission light L1 is emitted to the observation target S in a wide area, a projection image P can be displayed on the observation target S in a state in which a sufficient amount of the detection target light L3 is secured. In addition, the emission positions of the emission light L1 and the projection light L2 on the observation target S coincide with each other, and a process of determining the emission position of the projection light L2 is not necessary on the control unit 6 side, and accordingly, an arithmetic operation for reflecting results of the detection of the detection target light L3 in the projection image P is also simplified.

In addition, in the observation device 1, the optical axis of the optical scanning system 4 including the scanning mirror 10 and the optical axis of the light guide optical system G coincide with each other. For this reason, the device configuration is further simplified. In addition, even in a case in which the observation target moves in the direction of the optical axis, an influence on the observation can be reduced. In this way, the range of an operation distance of the observation device 1 can be broadened.

In addition, in this embodiment, the wavelength of the emission light L1 is 400 nm to 810 nm and is a wavelength enabling excitation of a fluorescent material. By selecting such a wavelength, a fluorescent material can be excited by the emission light L1, and fluorescent observation of the observation target S can be performed. In addition, in this wavelength band, representative fluorescent materials such as indocyanine green, methylene blue, fluorescein, and 5-aminolevulinic acid can be excited using the emission light L1.

In addition, in this embodiment, a single point sensor is used as the optical detector 5. In this way, a detection rate in the optical detector 5 can be raised, and real-time processing of the projection light L2 in the control unit 6 can be performed.

Second Embodiment

Figure 3:
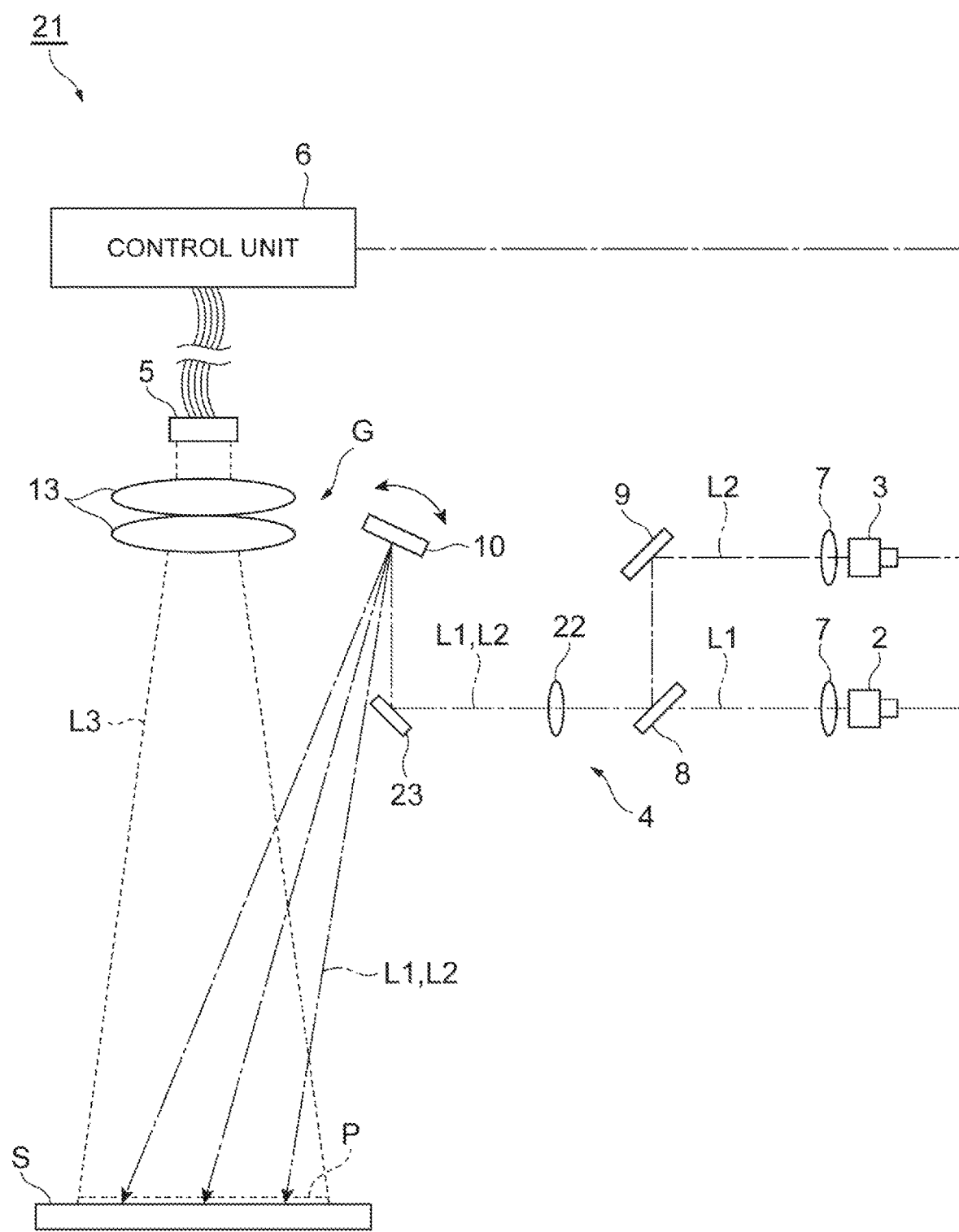
FIG. 3 is a schematic configuration diagram illustrating an observation device according to a second embodiment.

FIG. 3 is a schematic configuration diagram illustrating an observation device according to a second embodiment. As illustrated in the same drawing, in the observation device 21 according to the second embodiment, the optical axis of an optical scanning system 4 including a scanning mirror 10 and the optical axis of a light guide optical system G do not coincide with each other, which is different from the first embodiment.

More specifically, in the optical scanning system 4 of the observation device 21, the beam splitter 12 is not disposed, and emission light L1 and projection light L2 guided to the same optical path in a dichroic mirror 8 and a mirror 9 are condensed by a condensing lens 22, are reflected by a mirror 23, and are incident to the scanning mirror 10. The emission light L1 and the projection light L2 reflected by the scanning mirror 10 are incident to an observation target S with a predetermined inclination with the same optical path maintained. Then, detection target light L3 that is generated in the observation target S in accordance with emission of the emission light L1 is guided to an optical detector 5 by an observation lens 13 of the light guide optical system G without it passing through the scanning mirror 10.

Also in such an observation device 21, similar to the first embodiment, the device configuration is simplified, and a projection image P can be displayed on the observation target S in a state in which a sufficient amount of the detection target light L3 is secured. In addition, an arithmetic operation for reflecting results of the detection of the detection target light L3 in the projection image P becomes simple as well. Furthermore, in this embodiment, the optical axis of the optical scanning system 4 including the scanning mirror 10 and the optical axis of the light guide optical system G do not coincide with each other. In this way, an optical device splitting the emission light L1 and the projection light L2 and the detection target light L3 are not necessary, and accordingly, a sufficient amount of the detection target light L3 can be secured.

In addition, in the second embodiment, the optical axis of the optical scanning system 4 and the optical axis of the light guide optical system G do not coincide with each other, and it may also be considered that the range of an operation distance is narrower than that of the first embodiment. Thus, in the second embodiment, before the emission light L1 and the projection light L2 are emitted, it is preferable to perform an adjustment step of adjusting a distance between the observation device 21 and an observation target S within the range of the operation distance. In this adjustment step, for example, projection light L2 is emitted from the observation device 21 to an observation target S, and a distance between the observation device 21 and the observation target S is changed for being located at a position at which the projection light L2 can be visually recognized clearly. By performing this adjustment step, the projection light L2 can be emitted to the observation target S at the operation distance of the observation device 21.

Third Embodiment

Figure 4:
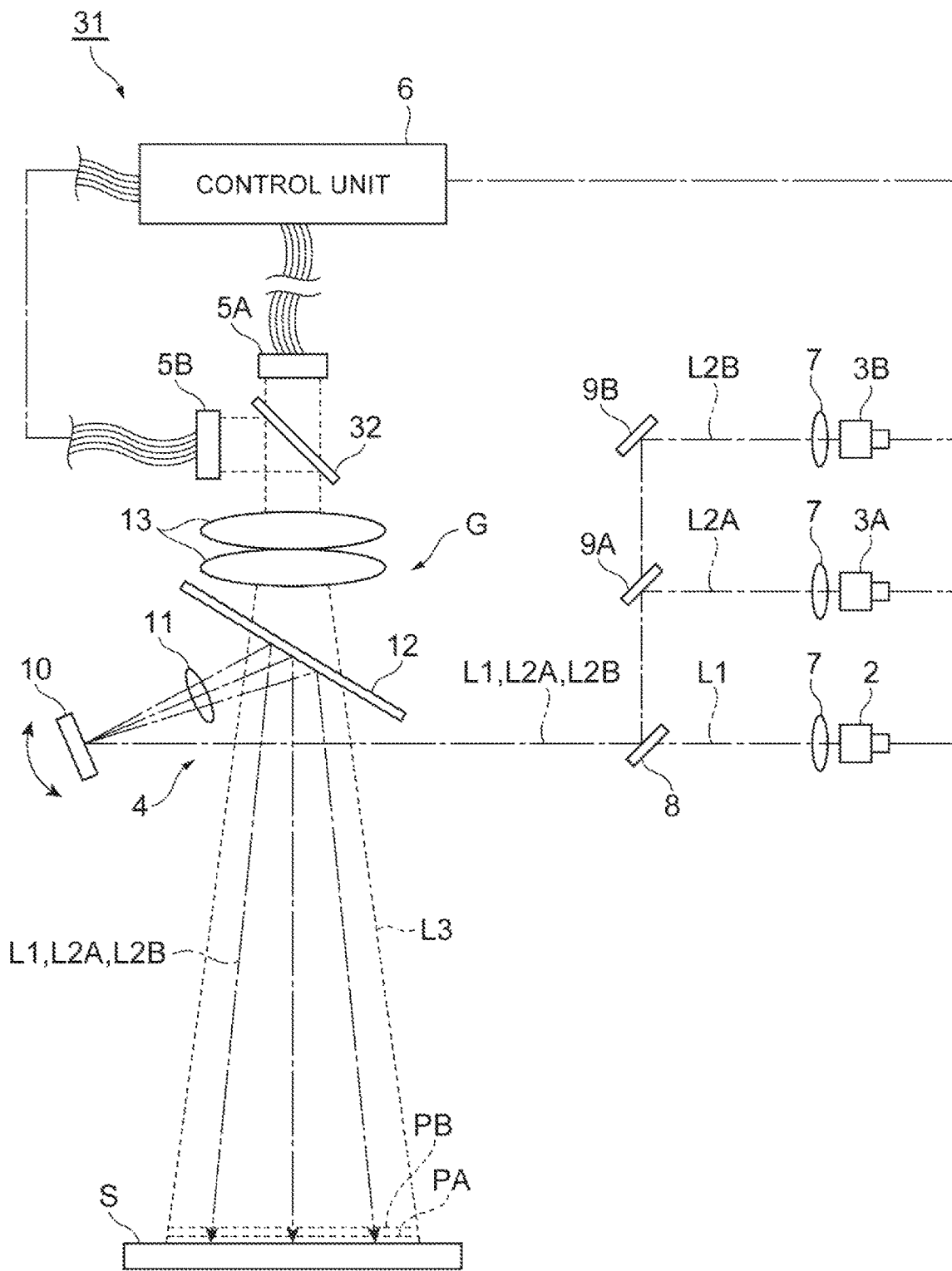
FIG. 4 is a schematic configuration diagram illustrating an observation device according to a third embodiment.

FIG. 4 is a schematic configuration diagram illustrating an observation device according to a third embodiment. The observation device 31 illustrated in the same drawing is configured as a device that simultaneously performs observation of positions of blood vessels within a biological tissue in addition to the fluorescent observation of the biological tissue described above. More specifically, the observation device 31 includes a first projection light source 3A and a second projection light source 3B and a first optical detector 5A and a second optical detector 5B, which is different from the first embodiment.

In a case in which observation of positions of blood vessels is performed, it is preferable that emission light L1 has a wavelength that can be absorbed by the blood vessels (or blood) inside an observation target S. In this case, for example, the wavelength of the emission light L1 is selected from a band of 735 nm to 850 nm. In a case in which fluorescent observation and observation of positions of blood vessels are simultaneously performed, it is preferable that the emission light L1 has a wavelength that can be absorbed by blood vessels (or blood) and excites a fluorescent material. For example, in a case in which fluorescent observation using indocyanine green as a fluorescent material and observation of positions of blood vessels are simultaneously performed, for example, a light source that outputs light having a wavelength of 785 nm is used as the emission light source 2.

The first projection light source 3A and the second projection light source 3B, for example, output light having a band of 380 nm to 780 nm that is a visible region. The first projection light source 3A outputs projection light L2A used for projecting a distribution of a fluorescent material, and the second projection light source 3B outputs projection light L2B used for projecting blood vessels (or a blood flow). For this reason, it is preferable that the wavelength of the projection light L2A output from the first projection light source 3A and the wavelength of the projection light L2B output from the second projection light source 3B are different from each other. In this embodiment, the first projection light source 3A, for example, is a light source that outputs light including a wavelength of green to yellow (for example, a wavelength of 580 nm), and the second projection light source 3B, for example, is a light source that outputs light including red (for example, a wavelength of 650 nm).

The projection light L2A and the projection light L2B have the same optical path as the emission light L1 using a dichroic mirror 8 and mirrors 9A and 9B and are scanned to an observation target S by the optical scanning system 4 with the state maintained. In this embodiment, a fluorescent material inside the observation target S is excited in accordance with incidence of the emission light L1, whereby fluorescence is generated. In addition, reflectance for the emission light L1 for an observation target S is different in accordance with presence/absence of blood vessels at an emission position of the emission light L1. At a position at which the blood vessels are present, the reflectance for the emission light L1 becomes relatively low in accordance with the influence of absorption according to the blood vessels. At a position at which no blood vessel is present, there is no influence of absorption according to blood vessels, and accordingly, the reflectance for the emission light L1 become relatively high.

Each of the first optical detector 5A and the second optical detector 5B is a single point sensor, for example, configured by a photo-diode, an avalanche photo-diode, a photomultiplier tube, a SiPM, or the like. In this embodiment, fluorescence generated in the observation target S in accordance with emission of emission light L1 and emission light L1 reflected by the observation target S become detection target light L3. In a light guide optical system G, a beam splitter 32 that splits the emission light L1 and the fluorescence in the detection target light L3 is disposed. The beam splitter 32, for example, is a dichroic mirror. The first optical detector 5A detects fluorescence spit by the beam splitter 32 and outputs a detection signal (information representing a result of detection) to the control unit 6. In addition, the second optical detector 5B detects emission light L1 spit by the beam splitter 32 and outputs a detection signal (information representing a result of detection) to the control unit 6.

When information representing detection results is received from the first optical detector 5A and the second optical detector 5B, the control unit 6 controls the intensity of the projection light L2A generated from the first projection light source 3A and the intensity of the projection light L2B generated from the second projection light source 3B on the basis of the detection results. In this way, projection image PA representing a position at which fluorescence is generated and a projection image PB representing a position at which blood vessels are detected are projected onto the surface of the observation target S.

Also in such an observation device 31, similar to the first embodiment, the device configuration is simplified, and the projection images PA and PB can be displayed on the observation target S in a state in which a sufficient amount of the detection target light L3 is secured. In addition, an arithmetic operation for reflecting detection results of the detection target light L3 in the projection images PA and PB is simplified.

In this embodiment, although the observation device 31 simultaneously performing fluorescence observation and observation of positions of blood vessels, which is acquired by modifying the first embodiment, has been illustrated as an example, a modification similar thereto may be applied to the second embodiment. In addition, in the first embodiment and the second embodiment, although the observation target S is a biological tissue into which a fluorescent material has been injected, and a device allowing observation of a state of the biological tissue in real time through fluorescence observation as the observation device 1 and the observation device 21 has been illustrated as an example, they are not limited thereto. Each of the observation devices 1 and 21 may have a configuration for detecting blood vessels inside an observation target S as described in the third embodiment instead of the configuration for performing fluorescence observation.

Fourth Embodiment

Figure 5:
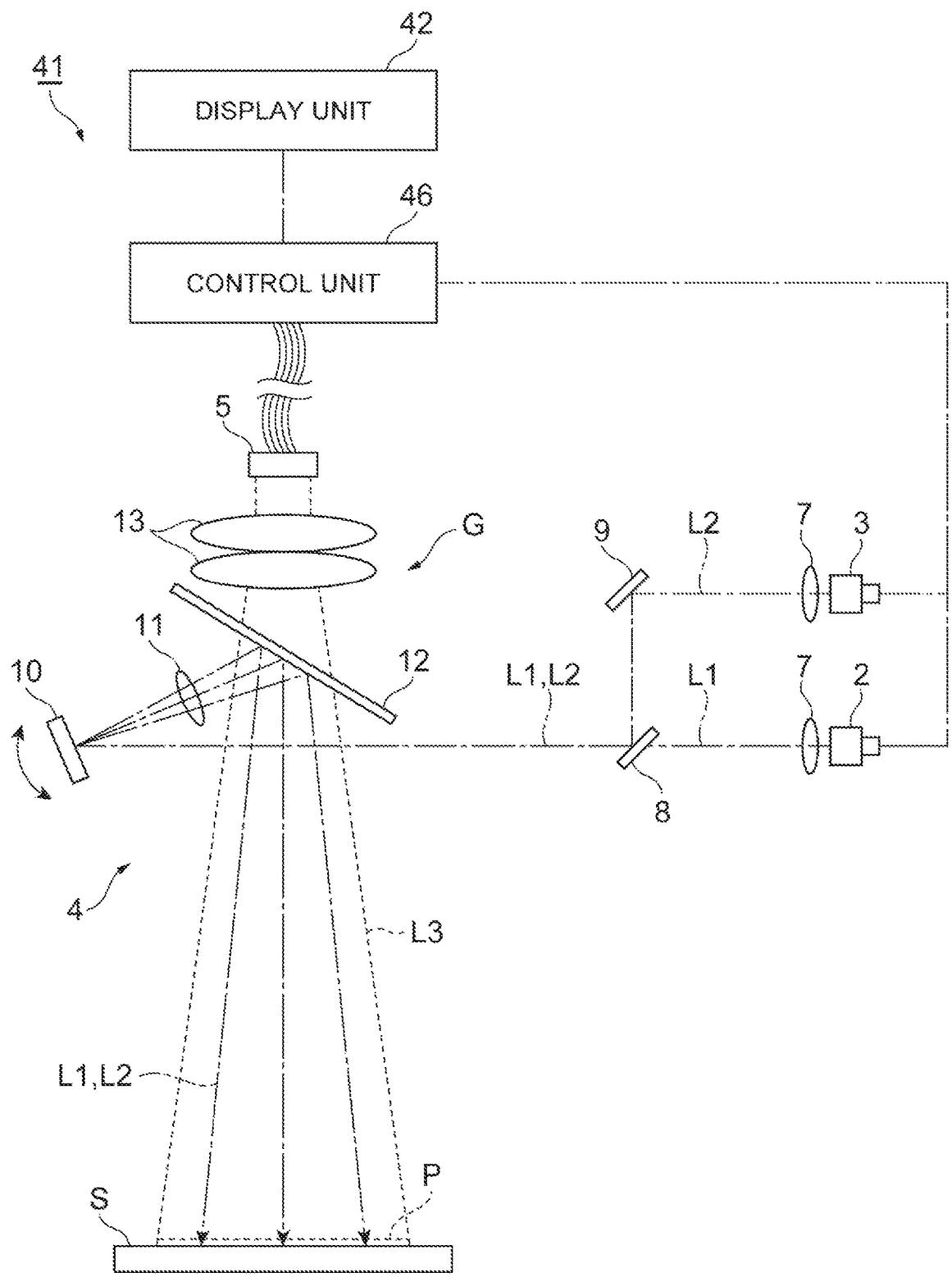
FIG. 5 is a schematic configuration diagram illustrating an observation device according to a fourth embodiment.

FIG. 5 is a schematic configuration diagram illustrating an observation device according to a fourth embodiment. The observation device 41 illustrated in the same drawing is configured as a device that generates an image based on a result of detection of detection target light L3 and performs display of the generated image and the like. More specifically, the observation device 41 includes a display unit 42, and a control unit 6 has a function as an image generating unit generating an image, which is different from the embodiments described above. In a conventional observation device, there are cases in which the detected intensity of fluorescence becomes insufficient for acquiring an image by imaging an emission area while emitting light from an infrared excitation light source toward an affected part. In contrast to this, in this embodiment, fluorescence is detected with high sensitivity, and an image based on a result of the detection can be acquired.

The display unit 42, for example, is a display and is electrically connected to the control unit 6. The display unit 42 displays various images generated by the control unit 6. The display unit 42 may simultaneously display images of different kinds, and a superimposed image in which images of different kinds are overlapped with each other may be displayed.

The control unit 6 as an image generating unit receives information representing a result of detection of detection target light L3 from an optical detector 5 and generates an image in which the result of detection is associated with an angle of a scanning mirror 10. Then, the control unit 6 stores the generated image as a still screen or a moving image in a storage unit such as a hard disk or the like and outputs the generated image to the display unit 42 as is necessary. The control unit 6 may transmit data stored as a still screen or a moving image to an external device through a communication interface or store the data in an external storage medium such as a USB memory or the like through a data input/output unit.

The observation device 41, similar to other embodiments, may control the intensity of projection light L2 generated from a projection light source 3 on the basis of a result of detection of detection target light L3 and form a projection image P on which the result of detection is reflected on the surface of an observation target S. The control of the intensity of the projection light L2 is performed in accordance with conditions such as a type of observation target S, a type of fluorescent material, and a wavelength of the projection light L2.

Figure 6:
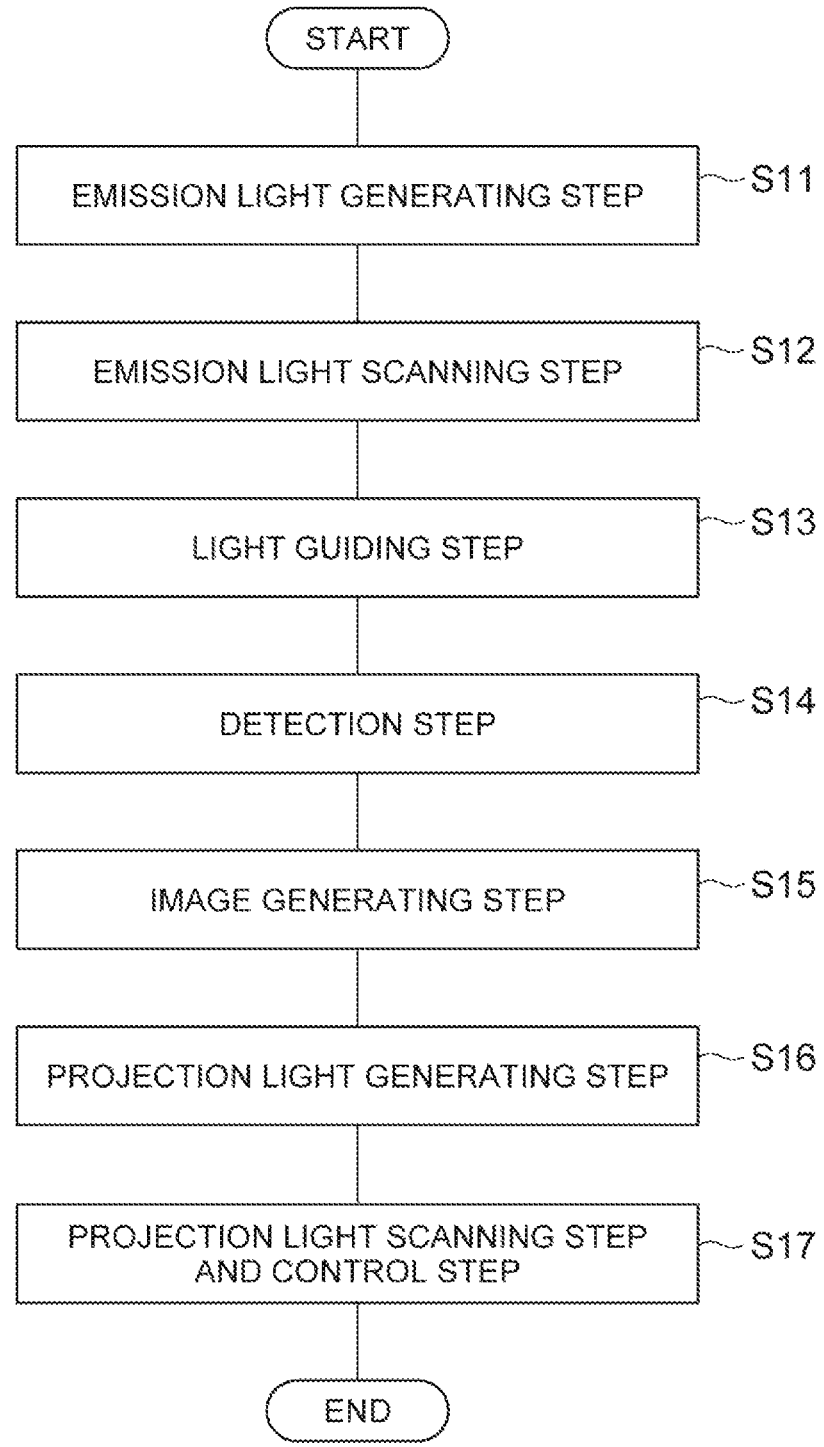
FIG. 6 is a flowchart illustrating an operation of the observation device illustrated in FIG. 5.

FIG. 6 is a flowchart that illustrates an operation of the observation device 41. As illustrated in the same drawing, in the observation device 41, when an operation for starting observation is input, emission light L1 is generated from an emission light source 2 (Step S11: an emission light generating step (first light generating step)). The emission light L1 is guided to an optical scanning system 4 and is scanned toward an observation target S by a scanning mirror 10 (Step S12: an emission light scanning step (an optical scanning step)). In accordance with the emission and the scanning of the emission light L1, detection target light L3 is generated in the observation target S.

Next, in the observation device 1, the detection target light L3 that is generated by the observation target S is guided to the optical detector 5 without it passing through the scanning mirror 10 (Step S13: a light guiding step). The detection target light L3 that is guided in the light guiding step S13 is detected by the optical detector 5 (Step S14: a detection step). Then, information representing a result of detection of the detection target light L3 is output to the control unit 6, and an image is generated on the basis of the result of detection of the detection target light L3 that is acquired by the optical detector 5 (Step S15: an image generating step). Various images generated in the image generating step S15 are stored in a storage unit or is displayed on the display unit 42.

Next, in the observation device 1, projection light L2 is generated from the projection light source 3 (Step S15: a projection light generating step (a second light generating step)). The projection light L2 is guided to an optical path that is the same as that of the emission light L1 in the optical scanning system 4. The projection light L2 is scanned toward the observation target S by the scanning mirror 10 with the same optical path as that of the emission light L1 maintained, and the intensity of the projection light L2 is controlled on the basis of a result of detection of the detection target light L3 that is acquired by the optical detector 5 (Step S16: a projection light scanning step (optical scanning step) and a control step). In this way, a projection image P on which the result of detection of the detection target light L3 is reflected is formed on the surface of the observation target S.

Also in such an observation device 41, similar to the embodiment described above, the device configuration is simplified, and a projection image P can be displayed on the observation target S in a state in which a sufficient amount of the detection target light L3 is secured. In addition, an arithmetic operation for reflecting results of the detection of the detection target light L3 in the projection image P becomes simple as well. Furthermore, the observation device 41 includes the control unit (image generating unit) 6 that generates an image on the basis of a result of detection of the detection target light L3. In this way, display of a result of detection on the display unit 42, storage of a result of detection in an external storage device, or the like can be performed.

In the fourth embodiment, the generated image based on a result of detection of detection target light L3 may be configured to displayed or stored without performing emission of projection light L2. In addition, in the fourth embodiment, the field of view (observation range) of the light guide optical system G may be set smaller than the scanning range of the emission light L1 according to the optical scanning system 4.

Other Modified Examples

The present invention is not limited to the embodiments described above. For example, in the embodiments described above, although fluorescence having a wavelength outside the visible range is illustrated to be generated in the observation target S in accordance with the emission light L1, the present invention can be applied also to a case in which fluorescence having a wavelength of the visible range is generated, a case in which weak fluorescence that is difficult to visually recognized is generated, a case in which a plurality of fluorescent materials are injected to an observation target S, and the like. In addition, in the embodiments described above, although a biological tissue is illustrated as an observation target S, and observation of fluorescence generated from an observation target S, observation of blood vessels inside an observation target S, and the like have been illustrated as examples, the observation target and the observation example are not limited to these. For example, the observation target S may be a picture having a rough sketch hidden inside. In such a case, for example, by detecting a state of the hidden rough sketch in accordance with changes in the reflectance of the emission light L1, a projection image P according to a result of the detection can be projected into a picture.

REFERENCE SIGNS LIST 1, 21, 31, 41 Observation device
2 Emission light source (first light source)
3, 3A, 3B Projection light source (second light source)
4 Optical scanning system
6 Control unit, image generating unit
10 Scanning mirror (optical scanning device)
5, 5A, 5B Optical detector
G Light guide optical system
L1 Emission light
L2, L2A, L2B Projection light
L3 Detection target light
S Observation target

The invention claimed is:

1. A device comprising:
   a first light source configured to generate emission light;
   a second light source configured to generate projection light;
   an optical scanner configured to scan the emission light and the projection light toward an observation target along the same optical path;
   a light guide optical system configured to guide detection target light generated in the observation target in accordance with emission of the emission light without it passing through the optical scanner;
   an optical detector configured to detect the detection target light guided by the light guide optical system; and
   a controller configured to control an intensity of the projection light on the basis of a result of the detection of the detection target light such that a projected image incorporating the result of the detection of the detection target light is formed on a surface of the observation target.

2. The device according to claim 1, wherein an optical axis of an optical scanning system including the optical scanner and an optical axis of the light guide optical system coincide with each other.

3. The device according to claim 1, wherein an optical axis of an optical scanning system including the optical scanner and an optical axis of the light guide optical system do not coincide with each other.

4. The device according to claim 1, wherein the emission light is excitation light.

5. The device according to claim 4, wherein a wavelength of the emission light is 400 nm to 810 nm.

6. The device according to claim 1, wherein a wavelength of the emission light is a wavelength that can be absorbed by the observation target.

7. The device according to claim 6, wherein the wavelength of the emission light is 735 nm to 850 nm.

8. The device according to claim 1, wherein a wavelength of the projection light is a wavelength different from a wavelength of the emission light.

9. The device according to claim 8, wherein the wavelength of the projection light is 380 nm to 780 nm.

10. The device according to claim 1, wherein the optical detector is a single point sensor.

11. The device according to claim 1, further comprising an image generator configured to generate the projected image on the basis of the result of the detection of the detection target light.

12. The device according to claim 1, wherein a field of view of the light guide optical system includes a scanning range of the emission light according to the optical scanner.

13. A method comprising:
    generating emission light;
    generating projection light;
    scanning the emission light and the projection light toward an observation target along the same optical path using an optical scanner;
    guiding detection target light generated in the observation target in accordance with emission of the emission light without it passing through the optical scanner using a light guide optical system;
    detecting the detection target light guided by the light guide optical system using an optical detector; and
    controlling an intensity of the projection light on the basis of a result of the detection of the detection target light such that a projected image incorporating the result of the detection of the detection target light is formed on a surface of the observation target.

14. The method according to claim 13, wherein an optical axis of an optical scanning system including the optical scanner and an optical axis of the light guide optical system are caused to coincide with each other.

15. The method according to claim 13, wherein an optical axis of an optical scanning system including the optical scanner and an optical axis of the light guide optical system are caused not to coincide with each other.

16. The method according to claim 13, wherein the emission light is set as excitation light.

17. The method according to claim 16, wherein a wavelength of the emission light is set to be 400 nm to 810 nm.

18. The method according to claim 13, wherein a wavelength that can be absorbed by the observation target is set as a wavelength of the emission light.

19. The method according to claim 18, wherein the wavelength of the emission light is set to be 735 nm to 850 nm.

20. The method according to claim 13, wherein a wavelength different from a wavelength of the emission light is set as a wavelength of the projection light.

21. The method according to claim 20, wherein the wavelength of the projection light is set to be 380 nm to 780 nm.

22. The method according to claim 13, wherein a single point sensor is used as the optical detector.

23. The method according to claim 13, wherein a scanning range of the emission light according to the optical scanner is included in a field of view of the light guide optical system.

* * * * *